United States Patent [19]

Takaya et al.

[11] Patent Number: 5,631,345
[45] Date of Patent: May 20, 1997

[54] PROCESS FOR PRODUCING OPTICALLY ACTIVE POLYKETONE

[75] Inventors: Hidemasa Takaya, deceased, late of Shiga, by Miyoko Takaya, Chikako Takaya, Haruko Takaya, heirs; Kyoko Tamao, Kyoto; Naomasa Sato, Aichi, all of Japan

[73] Assignee: Takasago International Corporation, Tokyo, Japan

[21] Appl. No.: 614,995

[22] Filed: Mar. 13, 1996

[30] Foreign Application Priority Data

Mar. 13, 1995 [JP] Japan .................................... 7-079367

[51] Int. Cl.$^6$ .................................................. C08G 67/02
[52] U.S. Cl. ..................... 528/392; 525/539; 502/162; 502/167; 430/321
[58] Field of Search .................... 528/392; 525/539; 502/162, 167; 430/321

[56] References Cited

FOREIGN PATENT DOCUMENTS

| 0403188 | 12/1990 | European Pat. Off. |
| 0614903 | 9/1994 | European Pat. Off. |

OTHER PUBLICATIONS

American Chemical Society, Polymer Preprints, vol. 35 No. 1 Mar. 1994.
"Stero–and Enantioselective Alternating Copolymerization of α–Olefins with Carbon Monoxide. Synthesis of Chiral Polymers", Macromolecules 1994, 27, 2694–2700.
"regio–, Staro–, and Enantioselective Alternating Copolymerization of Propene with Carbon Monoxide", Macromolecules 1994, 27, 4436–4440.

Primary Examiner—Samuel A. Acquah
Attorney, Agent, or Firm—Sughrue, Mion, Zinn, Macpeak & Seas

[57] ABSTRACT

A process for producing optically active polyketone which comprises allowing a mono-substituted ethylene to react with carbon monoxide in the presence of a palladium-phosphine complex formed from a phosphine represented by the following general formula (I)

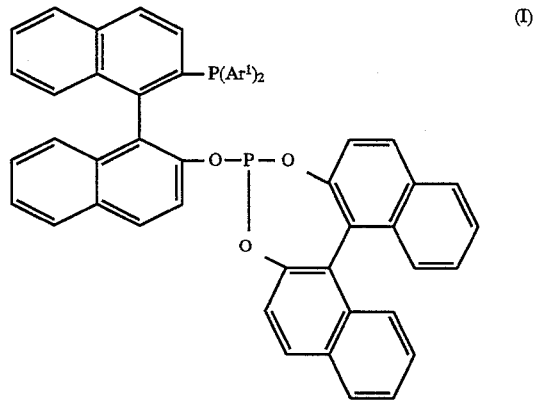

(wherein $Ar^1$ is a phenyl group which may be substituted with one or more substituent groups selected from a lower alkyl group, a lower alkoxy group and a halogen) and a palladium salt. An isotactic (stereoregular) optically active polyketone having high molecular weight (Mn) in which the direction of a mono-substituted ethylene against ketone is a head to tail type (positional regularity) can be produced efficiently by a simple and easy process for the copolymerization of propylene, styrene or the like mono-substituted ethylene with carbon monoxide.

4 Claims, No Drawings

PROCESS FOR PRODUCING OPTICALLY ACTIVE POLYKETONE

FIELD OF THE INVENTION

This invention relates to a process for the production of an optically active polyketone effected by the polymerization of propylene, styrene or a like mono-substituted ethylene with carbon monoxide. More particularly, it relates to a process for the production of an optically active polyketone in which a mono-substituted ethylene and carbon monoxide are copolymerized in completely alternating fashion and the direction of the mono-substituted ethylene against ketone is head to tail type and isotactic.

Making use of its characteristics regarding structural regularity, such a type of polyketone is applied to chromatographic and separation membrane materials for use in the separation and purification of optically active substances and ketone dipole-based piezoelectric pyroelectric materials and ferroelectric materials. Its application to biodegradable and photodegradable polymers having excellent mechanical strength is also expected.

BACKGROUND OF THE INVENTION

Techniques for a production of a polyketone from ethylene, propylene or the like α-olefin and carbon monoxide are well known.

For example, M. M. Brubaker et al. have reported a process for the production of a polyketone from ethylene and carbon monoxide in the presence of a radical initiator (*J. Amer. Chem. Soc.*, 74, 1509 (1952)). Also, U.S. Pat. No. 2,577,208 (1951) discloses a process for the production of a polyketone from ethylene and carbon monoxide in the presence of a nickel catalyst.

However, since these polyketone production processes require reaction under a high pressure and the reaction of ethylene with carbon monoxide has no regularity, the resulting polyketone has low crystallinity and poor mechanical strength.

The term "regularity of reaction" as used herein firstly relates to the reaction order of a mono-substituted ethylene and carbon monoxide. The first case is as follows: when a mono-substituted ethylene and carbon monoxide do not react with each other in alternating fashion, a poly-substituted-ethylene moiety in which the mono-substituted ethylene molecules alone are polymerized is formed and carbon atoms having substituent groups in this moiety lose asymmetry, so that the resulting polyketone shows reduced optical activity.

The second case is regularity of the binding mode of a mono-substituted ethylene to carbonyl group (positional regularity). This is divided into a head to a head type, a head to tail type and a tail to tail type. The reaction is regular when the head to tail type binding is perfectly made.

The third case is a regularity formed by the binding mode of polymer-specific substituent groups (stereoregularity). Isotactic and syndiotactic are regular, but a completely random case is called atactic which is irregular.

The fourth case is chirality of newly formed asymmetric carbon. When a mono-substituted ethylene and carbon monoxide copolymerize in alternating fashion, carbon atoms to which substituent groups are linked become asymmetric carbons and a polymer is constituted from only one antipode, the resulting polyketone is isotactic and such a polyketone becomes an optically active polymer. When chirality is formed alternately, the polymer becomes syndiotactic having a relatively small angle of rotation.

A. Sen et al. have reported a polymerization reaction of an olefin and carbon monoxide in which $[Pd(CH_3CN)_4](BF_4)_2(PPh_3)_n$ (n=1 to 3) is used as a catalyst (*J. Amer. Chem. Soc.*, 104, 3520 (1982)). According to this method, olefin and carbon monoxide are polymerized by alternating reaction, thus achieving the first case of the aforementioned regularities of reaction, but still leaving other regularities unsettled.

NL 84 03,035 (1984), EP 121,965 (1984) and EP 181,014 (1984) disclose polyketone production processes which use a complex of Pd(II), Co(II) or Ni(II) with a divalent ligand represented by $RR_1M(CR_4R_5)MR_2R_3$ (wherein M represents an element from P, As or Sb, each of R, $R_1$, $R_2$ and $R_3$ represents a hydrocarbon radical and each of $R_4$ and $R_5$ represents hydrogen or a hydrocarbon radical which has no steric hindrance).

Also, a copolymerization reaction in which a complex with a nitrogen-containing bidentate ligand such as bipyridine is used as a catalyst has been disclosed in JP-A-62-131025 (the term "JP-A" as used herein means an "unexamined published Japanese patent application").

Making use of such bidentate ligand complexes, processes for the production of a polyketone from a substituted ethylene such as propylene, styrene or the like and carbon monoxide have been disclosed (EP 229,408 (1986), JP-A-62-131025). For example, M. Barsacchi et al. (*Angew. Chem. Int. Ed. Engl.*, 30, 989 (1991)) have carried out copolymerization of styrene and carbon monoxide using (1,10-phenanthroline)Pd(p-$CH_3C_6H_4SO_3)_2$ as a catalyst and reported that the reaction was alternating and a syndiotactic binding mode was frequent as a stereochemistry of the substituent group. Polymerization of carbon monoxide with propylene or the like using a bidentate ligand complex has been disclosed in EP 376,364 (1989), EP 384,517 (1989), JP-A-2-189337 and JP-A-2-247223, but the aforementioned syndiotactic stereoselectivity is still low.

In addition, with regard to the synthesis of an optically active polyketone, the following report, for example, has recently been published.

A. Sen et al. have reported on the synthesis of an optically active polyketone by copolymerization of ethylene, propylene or styrene with carbon monoxide using a complex of an optically active bidentate ligand and divalent palladium as a catalyst (*Polym. Prepr.*, 35, 676,1994; *Macromolecules*, 27, 2694, 1994). According to these reports, in the case of the copolymerization of propylene with CO carried out using a ligand ((R)-(+)-BINAP) represented by the following formula

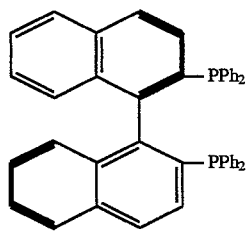

(R)-BINAP as an optically active ligand, the thus obtained polyketone showed a molecular weight of 3,100 and the turn over number (a value obtained by converting the yield of polymer per mole of catalyst into monomer mole numbers, to be referred to as "TO number" hereinafter) of 440. Positional selectivity of the reaction was 66% in the head to tail type, thus showing low positional regularity of the reaction (second regularity), and the $[\Phi]_D^{20}$ value was +25°

($CH_2Cl_2$). The term [Φ] is represented by the formula [Φ]=[α]×M/100 wherein [α] is specific rotation and M is molecular weight of the high molecular weight repeating unit. In the case of the copolymerization of styrene with carbon monoxide (to be referred to as "CO" hereinafter in some cases), the resulting polyketone has only 4% of isotactic bonding, thus showing extremely low stereoregularity.

G. Consiglio et al. have carried out copolymerization of propylene with CO using a complex composed of a bidentate ligand 2,4-pentadienylbis(diphenylphosphine) (to be referred to as "BDPP" hereinafter) represented by the following formula

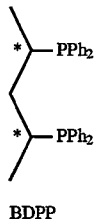

BDPP and divalent palladium and reported that about 83% of the product was head to tail type (Angew. Chem. Int. Ed. Engl., 31, 303, 1992). Though positional regularity (second regularity) of the reaction was improved, positional selectivity of the reaction was still low.

S. Bronco et al. have obtained a polyketone by carrying out copolymerization of propylene with CO using Pd(II) or Ni(II) as a catalyst in the presence of a diphosphine ligand (S)-6,6'-dimethylbiphenyl-2,2'-diyl)bis(dicyclohexylphoshine) (to be referred to as "(S)-BICHEP" hereinafter) represented by the following formula

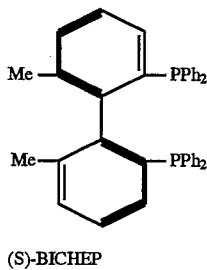

(S)-BICHEP and 1,4-naphthoquinone (Macromolecules, 27, 4436, 1994). That is, a polyketone having a number-average molecular weight (Mn) of 3,400 was obtained by carrying out 192 hours of reaction under a CO pressure of 42 atmospheres at 42° C. The TO number was 1,640, but the yield from propylene was 17.7% Th, which was low. The $[Φ]_D^{20}$ value was +18° (c, 0.97, $(CF_3)_2CHOH$), which was small, showing insufficient stereoregularity of the reaction.

Also, M. Brookhart et al. have reported on the relation of bidentate ligand to stereoregularity in the copolymerization of 4-tert-butylstyrene with CO produced using a Pd catalyst having the following bidentate ligand

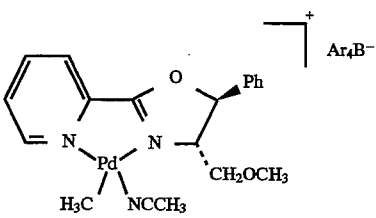

wherein Ar represents, 3,5-bistrifluoromethylphenyl group (J. Amer. Chem. Soc., 116, 3641, 1994). They report that 90% at the maximum is syndiotactic when the bidentate ligand is 2,2-bipyridine or 2,2-bipyrimidine, and an isotactic polyketone is obtained when an optically active bisoxazoline is used. Also, according to this report, a polyketone having a molecular weight (Mn) of 26,000 is obtained with a yield of 21.5% Th from p-tert-butylstyrene by carrying out 72 hours of copolymerization reaction of p-tert-butylstyrene at 25° C. under a CO pressure of 1 atmosphere using a catalyst of the following bidentate ligand in which R is i-Pr

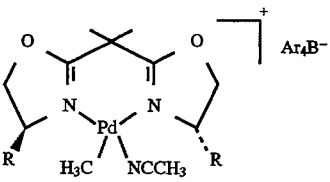

wherein Ar represents 3,5-bistrifluoromethylphenyl group). The TO number was 100 showing low catalytic activity. The $[Φ]_D^{20}$ value was −536°.

SUMMARY OF THE INVENTION

In view of the above, it therefore becomes an object of the present invention to provide a novel and practical process for the production of a polyketone which satisfies positional and stereostructural regularities of the reaction, namely an optically active polyketone which is polymerized in such a manner that it has markedly high positional regularity and stereoregularity such as completely alternating copolymerization of a mono-substituted ethylene and carbon monoxide, completely head to tail type direction of the mono-substituted ethylene against ketone and isotactic bonding.

With the aim of producing an optically active polyketone position-regularly and stereo-regularly polymerized from a mono-substituted ethylene and carbon monoxide, the inventors of the present invention have conducted intensive studies and found that an optically active polyketone which is polymerized in such a manner that it has markedly high stereoregularity such as completely alternating copolymerization of a mono-substituted ethylene and carbon monoxide, completely head to tail type direction of the mono-substituted ethylene against ketone and isotactic bonding can be produced when a complex formed from a specified axially asymmetric bidentate ligand represented by the following general formula (I) and palladium is used as a catalyst. The present invention has been accomplished on the basis of this finding.

Accordingly, the gist of the present invention resides in a process for the production of optically active polyketone which comprises, in the presence of a palladium-phosphine complex formed from a phosphine represented by the following general formula (I)

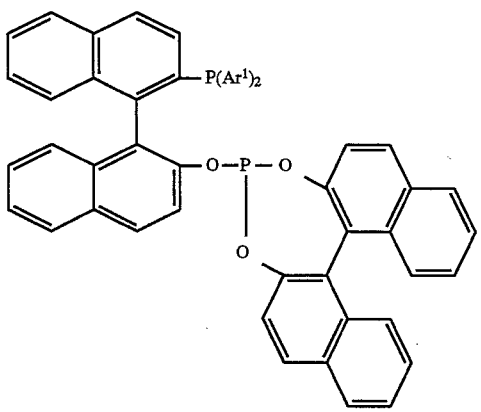

(I)

(wherein Ar¹ represents a phenyl group which may be substituted with one or more substituent groups selected from a lower alkyl group, a lower alkoxy group and a halogen) and a palladium salt, allowing a mono-substituted ethylene represented by the following general formula (II)

(II)

(wherein R¹ represents a branched- or straight-chain alkyl group which may be substituted, an aralkyl group or an aryl group which may be substituted with a lower alkyl group, a lower alkoxy group or a halogen atom, each having 1 to 9 carbon atoms) to react with carbon monoxide, thereby obtaining an optically active polyketone represented by the following general formula (III)

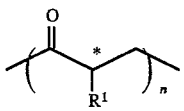

(III)

wherein R¹ is as defined above, and n is an integer of 10 to 10,000, preferably of 100 to 10,000.

Other objects and advantages of the present invention will be made apparent as the description progresses.

DETAILED DESCRIPTION OF THE INVENTION

The optically active polyketone of the present invention can be synthesized in accordance with a scheme represented by the following general formula (V)

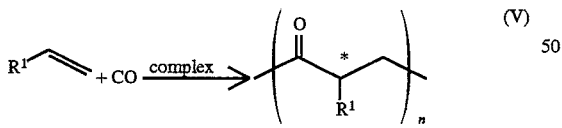

(V)

wherein R¹ represents a branched- or straight-chain alkyl group which may be substituted, an aralkyl group or an aryl group which may be substituted with a lower alkyl group, a lower alkoxy group or a halogen atom, each having 1 to 9 carbon atoms. In the present invention, the lower alkyl or lower alkoxy group preferably has 1 to 4 carbon atoms.

In one aspect of the present invention, R¹ is selected from a branched- or straight chain alkyl group, a lower alkyl-substituted phenyl group, a lower alkoxy-substituted phenyl group, a halogen-substituted phenyl group and a phenylalkyl group, each having 1 to 10 carbon atoms.

The aforementioned complex to be used in the present invention as a catalyst can be synthesized in accordance with a scheme represented by the following general formula (VI)

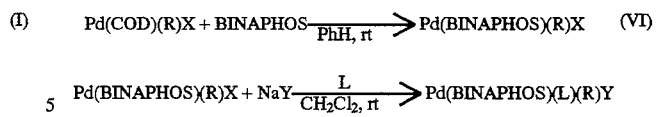

wherein R represents a branched- or straight-chain alkyl group which may be substituted, an aralkyl group or an aryl group which may be substituted, each having 1 to 10 carbon atoms, L is a coordination solvent, Y represents a counter anion and X represents a halogen atom.

Examples of the substituent group on alkyl or aryl group of R include lower alkyl groups having 1 to 4 carbon atoms such as methyl, ethyl, n-propyl, isopropyl and the like, halogen-substituted lower alkyl groups having 1 to 4 carbon atoms such as trifluoromethyl and the like, lower alkoxy groups having 1 to 4 carbon atoms such as methoxy, ethoxy and the like and halogen atoms such as fluorine, chlorine, bromine and the like.

For example, an alkylpalladium cyclooctadiene halide (Pd(COD)(R)X) dissolved in benzene is allowed to react with a ligand, 2-(diphenylphosphino)-1,1'-binaphthalen-2'-yl) (1,1'-binaphthalen-2,2'-yl)phosphite (to be referred to as "BINAPHOS" hereinafter), thereby obtaining a ligand-exchanged complex Pd(BINAPHOS)(R)X. This is then allowed to react with NaY in acetonitrile to effect anion exchange, thereby obtaining the intended complex of the present invention Pd(BINAPHOS)(L)(R)Y.

In the aforementioned scheme represented by the general formula (VI), X is selected generally from chlorine, bromine and iodine, of which chlorine is particularly preferred.

The bidentate ligand BINAPHOS is preferably an optically active BINAPHOS, more preferably an (R,S)-BINAPHOS or an (S,R)-BINAPHOS illustrated in the following.

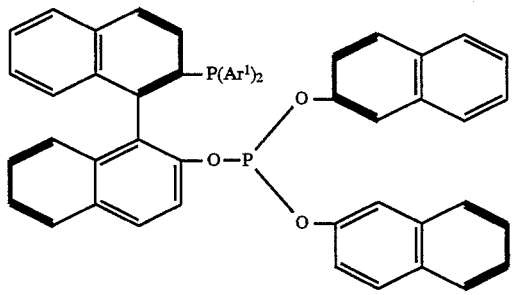

(R,S)-BINAPHOS

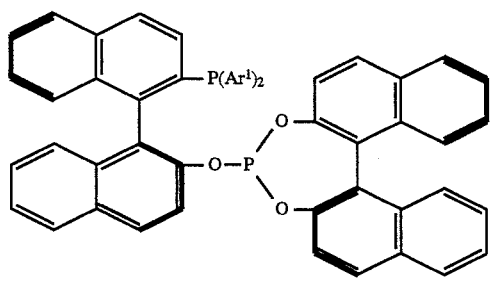

(S,R)-BINAPHOS

[In the above formulae, Ar¹ represents a phenyl group which may be substituted with one or more substituent groups selected from a lower alkyl group (e.g., methyl, ethyl, n-propyl, isopropyl, trifluoromethyl, etc.), a lower alkoxy group (e.g., methoxy, ethoxy, etc.), and a halogen (e.g., fluorine, chlorine, bromine, etc.).]

Ar$^1$ in the bidentate ligand BINAPHOS is a phenyl group which may be substituted, preferably phenyl, p-tolyl or the like group.

In the complex (Pd(BINAPHOS)(L)(R)Y) of the present invention, examples of Y include those which become counter anions of cations, such as $BF_4$, $B(Ar^2)_4$, $PF_6$, $ClO_4$ and the like, of which $B(Ar^2)_4$ is particularly preferred. Most preferably, Ar$^2$ is 3,5-bistrifluoromethylphenyl group.

In the complex of the present invention, R is a branched- or straight-chain alkyl group which may be substituted, an aralkyl group or an aryl group which may be substituted, each having 1 to 10 carbon atoms, preferably methyl or phenyl group.

In the aforementioned scheme represented by the general formula (VI), the coordination solvent (L) is selected from those which can dissolve the complexes (Pd(BINAPHOS)(L)(R)Y) and (Pd(BINAPHOS)(R)X) and coordinate to palladium. Their illustrative examples include nitriles such as acetonitrile, benzonitrile and the like, chlorides such as methylene chloride and the like, ethers such as tetrahydrofuran and the like and amines such as triethylamine and the like, of which acetonitrile is particularly preferred.

Illustrative examples of preferred complexes to be used in the present invention are shown in Table 1.

TABLE 1

| Complex No. | Ar$^1$ | R | L | Y |
|---|---|---|---|---|
| 1 | $C_6H_5$ | $CH_3$ | $CH_3CN$ | $B[3,5\text{-}(CF_3)_2C_6H_3]_4$ |
| 2 | $p\text{-}CH_3C_6H_4$ | $CH_3$ | $CH_3CN$ | $B[3,5\text{-}(CF_3)_2C_6H_3]_4$ |
| 3 | $p\text{-}ClC_6H_4$ | $CH_3$ | $CH_3CN$ | $B[3,5\text{-}(CF_3)_2C_6H_3]_4$ |
| 4 | $3,5\text{-}(CH_3)_2C_6H_3$ | $CH_3$ | $CH_3CN$ | $B[3,5\text{-}(CF_3)_2C_6H_3]_4$ |
| 5 | $C_6H_5$ | $C_2H_5$ | $CH_3CN$ | $B[3,5\text{-}(CF_3)_2C_6H_3]_4$ |
| 6 | $p\text{-}CH_3C_6H_4$ | $C_2H_5$ | $CH_3CN$ | $B[3,5\text{-}(CF_3)_2C_6H_3]_4$ |
| 7 | $C_6H_5$ | $CH_3$ | $CH_3CN$ | $BF_4$ |
| 8 | $p\text{-}CH_3C_6H_4$ | $CH_3$ | $CH_3CN$ | $BF_4$ |
| 9 | $C_6H_5$ | $CH_3$ | $C_6H_5CN$ | $B[3,5\text{-}(CF_3)_2C_6H_3]_4$ |
| 10 | $C_6H_5$ | $CH_3$ | $C_6H_5CN$ | $B[3,5\text{-}(CF_3)_2C_6H_3]_4$ |
| 11 | $C_6H_5$ | $C_4H_9$ | $CH_3CN$ | $B[3,5\text{-}(CF_3)_2C_6H_3]_4$ |
| 12 | $C_6H_5$ | $CH_3$ | $N(C_2H_5)_3$ | $B[3,5\text{-}(CF_3)_2C_6H_3]_4$ |
| 13 | $C_6H_5$ | $CH_3$ | $CH_2Cl_2$ | $B[3,5\text{-}(CF_3)_2C_6H_3]_4$ |
| 14 | $C_6H_5$ | $CH_3$ | THF | $B[3,5\text{-}(CF_3)_2C_6H_3]_4$ |

The mono-substituted ethylene to be used in the present invention is a mono-substituted ethylene having 3 to 12 carbon atoms, and its substituent group R$^1$ is a branched- or straight-chain alkyl group, an aralkyl group or an aryl group which may be substituted with a lower alkyl group, a lower alkoxy group or a halogen atom, each having 1 to 9 carbon atoms. Preferably, the substituent group R$^1$ is a branched- or straight-chain alkyl group which may be substituted, an aralkyl group or an aryl group which may be substituted, each having 1 to 9 carbon atoms. Examples of the substituent group on alkyl or aryl group include lower alkyl groups such as methyl, ethyl, propyl, butyl and the like, alkoxy groups such as methoxy, ethoxy, propoxy, butoxy and the like and halogen atoms such as chlorine, bromine, fluorine and the like.

Illustrative examples of the mono-substituted ethylene include propylene, 1-butene, 3-methyl-1-butene, 1-pentene, 1-hexene, 1-heptene, 1-octene, 3,7-dimethyl-1-octene, 3-(3', 4'-dimethoxyphenyl)-1-propylene, styrene, p-methylstyrene, p-ethylstyrene, p-propylstyrene, p-tert-butylstyrene, p-methoxystyrene, p-chlorostyrene and the like.

The optically active polyketone of the present invention can be produced by selecting a mono-substituted ethylene compound or a mixture of two or more mono-substituted ethylene compounds from the above illustrative examples as the starting material and subjecting the material to a polymerization reaction.

Illustrative examples of the polyketone include optically active poly-1-oxo-2-methyl-propane, poly-1-oxo-2-ethyl-propane, poly-1-oxo-2-propyl-propane, poly-1-oxo-2-isopropyl-propane, poly-1-oxo-2-butyl-propane, poly-1-oxo-2-pentyl-propane, poly-1-oxo-2-phenyl-propane, poly-1-oxo-2-(3',4'-dimethoxyphenyl)methyl-propane, poly-1-oxo-2-(p-methylphenyl)-propane, poly-1-oxo-2-(p-ethylphenyl)-propane, poly-1-oxo-2-(p-propylphenyl)-propane, poly-1-oxo-2-(p-tert-butylphenyl)-propane, poly-1-oxo-2-(p-methoxyphenyl)-propane, poly-1-oxo-2-(p-chlorophenyl)-propane and the like.

According to the present invention, the polymerization reaction may be carried out under a pressure of generally from 1 to 100 atmospheres, preferably from 1 to 50 atmospheres.

Illustrative examples of the solvent to be used in the polymerization reaction of the present invention are inert solvents which preferably include water, alcohols such as methanol, ethanol, isopropanol and the like, ethers such as diethyl ether, dibutyl ether, tetrahydrofuran and the like, nitro compounds such as nitromethane, nitrobenzene and the like, halogenated solvents such as dichloromethane, chloroform, dichloroethane, chlorobenzene and the like, and mixture solvents thereof.

By such a process of the present invention, an optically active polyketone having a head to tail type (%) of about 80% or more or 90% or more can be produced. Also, an isotactic (stereoregular) high molecular weight polyketone can be produced efficiently by a simple and easy process. According to the present invention, the TO number is large and the yield is high.

For example, as will be described later in EXAMPLES, a polyketone produced from propylene and carbon monoxide using a palladium complex catalyst having the aforementioned ligand (R,S)-BINAPHOS represented by the general formula (I) showed a markedly high molecular weight (Mn=65,300), and the TO number of the catalyst was 420 showing high catalytic activity. Also, since chemical shift of ketone carbons was found only at 212.5 ppm in its $^{13}$C-NMR spectrum, it was found that its head to tail type was 100% and positional regularity (second regularity) of the reaction of propylene with carbon monoxide was markedly high. In addition, the large $[\Phi]_D^{23}$ value of +40° (c, 0.51, $(CF_3)_2CHOH$) as its angle of rotation shows that the thus obtained polyketone is optically active, and the presence of chemical shift of ketone carbons only at 212.5 ppm shows that stereoregularity on the newly formed asymmetric carbon is sufficiently high.

Also, a polyketone produced for example from p-tert-butylstyrene and carbon monoxide using a palladium complex catalyst having the aforementioned ligand (R,S)-BINAPHOS represented by the general formula (I) showed a molecular weight (Mn) of 2,700, an angle of rotation value $[\Phi]_D^{23}$ of −454 and a TO number of 336. Yield of the polyketone from p-tert-butylstyrene was 43.5% which was markedly high.

EXAMPLES

Examples of the present invention are given below by way of illustration and not by way of limitation.

Instruments used herein for the measurement of various properties are as follows.

$^1$H-NMR and $^{13}$C-NMR:

Measured using JEOL EX-270 (manufactured by JEOL).

IR:

Measured using JASCO IR-810 (manufactured by JASCO).

Angle of rotation ([Φ]):

Measured using JASCO DIP-360 (manufactured by JASCO).

Mn (number-average molecular weight) and Mw (weight average molecular weight):

Measured by a gel permeation chromatography (GPC) using an instrument D-2520 GPC Integrator (manufactured by Hitachi).

Tm (melting point) and Tg (glass transition point):

Measured using a differential scanning calorimeter DSC50 (manufactured by Shimadzu).

Td (thermal decomposition starting temperature):

Measured using an apparatus for thermogravimetry TGA50 (manufactured by Shimadzu).

REFERENCE EXAMPLE 1

Synthesis of chloro(methyl)(1,5-cyclooctadiene)palladium (Pd(COD)MeCl)

One mol part of dichloro(1,5-cyclooctadiene)palladium ($PdCl_2(COD)$) was allowed to react with 2 mol parts of dimethyllithium cuprate ($LiCuMe_2$) to obtain dimethyl(1,5-cyclooctadiene)palladium ($PdMe_2(COD)$). This was subjected to a homogenization reaction with the same amount of dichloro(1,5-cyclooctadiene)palladium to obtain chloro(methyl)(1,5-cyclooctadiene)palladium. This can be synthesized also by a reaction of dichloro(1,5-cyclooctadiene)palladium with tetramethyltin (method of M. Rudler Chauvin et al., *J. Organomet. Chem.*, 134 (1977), 115).

REFERENCE EXAMPLE 2

Synthesis of (R,S)-BINAPHOS

This was obtained by a condensation reaction of (R)-2-(diphenylphosphinyl)-1,1'-binaphthalen-2'-ol with (S)-4-chloro-dinaphtho[2,1-d,1',2'-f][1,3,2]dioxaphosphepin in ether in the presence of triethylamine (method of Sasaki et al., *J. Am. Chem. Soc.*, 115, 7033 (1993)).

INVENTIVE EXAMPLE 1

To a benzene solution (0.5 ml) of Pd(COD)MeCl (3.0 mg) obtained in Reference Example 1 was added a benzene solution (1 ml) of (R,S)-BINAPHOS (8.7 mg) obtained in Reference Example 2. The resulting solution was stirred at 20° C. for 1 hour and then benzene was evaporated. The thus obtained residue was dissolved in methylene chloride (1 ml) to which was subsequently added an acetonitrile solution (1 ml) of $NaB[3,5-(CF_3)_2C_6H_3]_4$ (10 mg). After 1 hour of stirring of this mixture at 20° C., methylene chloride and excess acetonitrile were removed. The thus obtained residue was dissolved in methylene chloride (2 ml), and the resulting solution was degassed and then stirred for 10 minutes in an atmosphere of carbon monoxide.

Thereafter, the reaction solution was transferred into an autoclave and, after charging with 3 atmospheres of propylene, stirred at 20° C. for 4 days under a carbon monoxide pressure of 20 atmospheres. The reaction mixture was mixed with 100 ml of methanol, and the thus formed solid matter was collected by filtration using a glass filter to obtain 333.4 mg of a copolymer of interest. Yield of the polyketone based on the used propylene was 127%, and the TO number was 420. Its $^{13}$C-NMR spectrum showed that the ratio of head to tail type was 100%.

Physical properties of the thus obtained copolymer are as follows.

Mw=104,400, Mn=65,300, Mw/Mn=1.6 n=933

Tm=164° C., Tg=8° C., Td=213° C.

$^1$H-NMR; 1.03 (d, j=6.93 Hz, 3H), 2.52 (dd, j=16.83 and 1.98 Hz, 1H), 2.88–3.09 (m, 2H)

$^{13}$C-NMR; 16.5, 40.1, 44.8, 212.5

IR (Nujol); 1705 (CO) cm$^{-1}$ $[\Phi]_D^{23}$; +40° (c, 0.5, $(CF_3)_2CHOH$)

INVENTIVE EXAMPLE 2

A 715 mg portion of a copolymer of interest was obtained by repeating the reaction and after-treatment of Inventive Example 1 except that p-tert-butylstyrene (1.64 g, 10.2 mmol) was used instead of propylene, and CO pressure and reaction temperature were changed to 40 atmospheres and 60° C., respectively. Yield of the polyketone based on the used p-tert-butylstyrene was 43.5%, and the TO number was 336.

Physical properties of the thus obtained copolymer are as follows.

Mw=3,800, Mn=2,700, Mw/Mn=1.4

Tg=106° C., Td=348° C.

$^1$H-NMR; 1.24 (s, 9H), 2.59–2.74 (m, 1H), 3.10–3.20 (m, 1H), 3.89–4.10 (m, 1H), 6.85 (d, j=8.25 Hz, 2H), 7.12 (d, j=8.25 Hz, 2H)

$^{13}$C-NMR; 31.3, 34.4, 45.6, 51.7, 125.6, 127.8, 134.4, 149.9, 207.0

IR (Nujol); 1711 (CO) cm$^{-1}$ $[\Phi]_D^{23}$; −454° (c, 0.50, $CH_2Cl_2$)

INVENTIVE EXAMPLE 3

A 218.6 mg portion of a copolymer of interest was obtained by repeating the reaction and after-treatment of Inventive Example 1 except that the pressure of propylene was changed to 1.9 atmospheres. Yield of the polyketone based on the used propylene was 131%, and the TO number was 275.

Physical properties of the thus obtained copolymer are as follows.

Mw=26,800, Mn=51,300, Mw/Mn=1.9

Tg=12° C., Tm=160° C., Td=206° C.

$^1$H-NMR, $^{13}$C-NMR and IR (Nujol); the same as the results of Inventive Example 1

$[\Phi]_D^{27}$; 35° (c, 0.51, $(CF_3)_2CHOH$)

INVENTIVE EXAMPLE 4

A 556.2 mg portion of a copolymer of interest was obtained by repeating the reaction and after-treatment of Inventive Example 1 except that the pressure of propylene was changed to 5 atmospheres. Yield of the polyketone based on the used propylene was 127%, and the TO number was 701.

Physical properties of the thus obtained copolymer are as follows.

Mw=34,500, Mn=73,400, Mw/Mn=2.1

Tg=15° C., Tm=162° C., Td=197° C.

$^1$H-NMR, $^{13}$C-NMR and IR (Nujol); the same as the results of Inventive Example 1

$[\Phi]_D^{27}$; 23° (c, 0.51, $(CF_3)_2CHOH$)

Thus, according to the present invention, an isotactic (stereoregular) optically active polyketone having high molecular weight (Mn) in which the direction of a mono-substituted ethylene against ketone is a head to tail type (positional regularity) can be produced efficiently by a simple and easy process for the copolymerization of propylene, styrene or the like mono-substituted ethylene with carbon monoxide.

Such a type of optically active polyketone can be expected as a polymer of chromatographic and separation membrane materials for use in the separation and purification of optically active substances and ketone dipole-based piezoelectric pyroelectric materials and ferroelectric materials.

While the invention has been described in detail and with reference to specific embodiments thereof, it will be apparent to one skilled in the art that various changes and modifications can be made therein without departing from the spirit and scope thereof.

What is claimed is:

1. A process for producing optically active polyketone which comprises reacting a mono-substituted ethylene represented by the following general formula (II)

 (II)

wherein $R^1$ represents a branched- or straight-chain alkyl group which may be substituted, an aralkyl group or an aryl group which may be substituted with a lower alkyl group, a lower alkoxy group or a halogen atom, each having 1 to 9 carbon atoms with carbon monoxide, thereby obtaining an optically active polyketone represented by the following general formula (III)

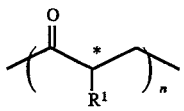 (III)

wherein $R^1$ is as defined above, and n is an integer of 10 to 10,000, said reacting being in the presence of a palladium-phosphine complex formed from a phosphine represented by the following general formula (I)

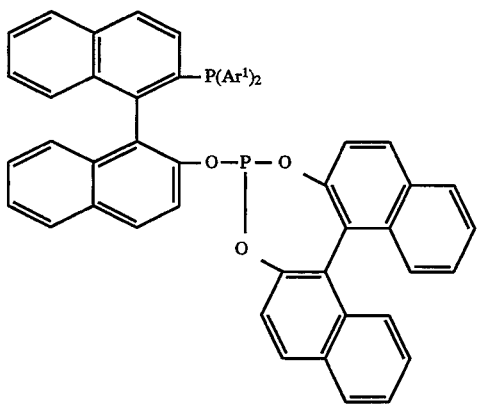 (I)

wherein $Ar^1$ represents a phenyl group which may be substituted with one or more substituent groups selected from a lower alkyl group, a lower alkoxy group and a halogen, and a palladium salt.

2. The process for producing optically active polyketone according to claim 1, wherein $R^1$ is selected from a branched- or straight chain alkyl group, a lower alkyl-substituted phenyl group, a lower alkoxy-substituted phenyl group, a halogen-substituted phenyl group and a phenylalkyl group, each having 1 to 10 carbon atoms.

3. The process for producing optically active polyketone according to claim 1, wherein the anion of said palladium-phosphine complex is selected from $BF_4$, $B(Ar^2)_4$ wherein $Ar^2$ is a phenyl group which may be substituted with at least one group selected from a lower alkyl group, a lower alkoxy group and a halogen atom, $PF_6$ and $ClO_4$.

4. The process for producing optically active polyketone according to claim 3, wherein the anion of said palladium-phosphine complex is an anion of the following formula (IV)

$B(Ar^2)_4$ (IV)

wherein $Ar^2$ is a 3,5-bistrifluoromethylphenyl group.

* * * * *